(12) United States Patent
Mediratta et al.

(10) Patent No.: US 11,523,679 B2
(45) Date of Patent: Dec. 13, 2022

(54) ORAL CARE DEVICE

(71) Applicants: Vinni Mediratta, Indore (IN); Sumit Dharampal Mediratta, Indore (IN)

(72) Inventors: Vinni Mediratta, Indore (IN); Sumit Dharampal Mediratta, Indore (IN)

( * ) Notice: Subject to any disclaimer, the term of this patent is extended or adjusted under 35 U.S.C. 154(b) by 611 days.

(21) Appl. No.: 16/583,326

(22) Filed: Sep. 26, 2019

(65) Prior Publication Data
US 2020/0093255 A1 Mar. 26, 2020

Related U.S. Application Data

(60) Provisional application No. 62/736,481, filed on Sep. 26, 2018.

(51) Int. Cl.
| | |
|---|---|
| *A46B 9/04* | (2006.01) |
| *A46B 15/00* | (2006.01) |
| *A61C 15/04* | (2006.01) |
| *A61B 5/0534* | (2021.01) |
| *A46B 9/08* | (2006.01) |
| *A61C 17/22* | (2006.01) |

(52) U.S. Cl.
CPC .......... *A46B 15/0012* (2013.01); *A46B 9/045* (2013.01); *A46B 9/08* (2013.01); *A46B 15/0002* (2013.01); *A46B 15/0081* (2013.01); *A61B 5/0534* (2013.01); *A61C 15/047* (2013.01); *A46B 2200/1066* (2013.01); *A61C 17/22* (2013.01)

(58) Field of Classification Search
CPC ........ A61C 17/22; A46B 9/04; A46B 15/0012
See application file for complete search history.

(56) References Cited

U.S. PATENT DOCUMENTS

| | | | |
|---|---|---|---|
| 10,064,711 B1* | 9/2018 | Richter | A61C 17/221 |
| 2007/0204413 A1* | 9/2007 | Kuznetsov | A61C 17/3472 |
| | | | 15/22.1 |
| 2010/0325828 A1* | 12/2010 | Braun | A46B 15/0008 |
| | | | 15/167.1 |
| 2013/0067670 A1* | 3/2013 | Liangco | A46B 9/06 |
| | | | 15/167.2 |
| 2013/0239349 A1* | 9/2013 | Knights | A46B 15/0038 |
| | | | 15/167.1 |
| 2014/0310900 A1* | 10/2014 | Curry | A46B 15/0004 |
| | | | 15/167.1 |

* cited by examiner

*Primary Examiner* — Michael D Jennings
(74) *Attorney, Agent, or Firm* — Robinson IP Law, PLLC

(57) ABSTRACT

An oral care device comprises a head portion and a handle portion. The head portion comprises at least one supporting arm and a base. The supporting arm extends from the base. A sensor is exposed from the supporting arm. The handle portion is configured to move relative to the head portion. The handle portion comprises a processor, wherein the processor is configured to receive signals from the sensor and analyze the signals received from the sensor.

20 Claims, 15 Drawing Sheets

ORAL CARE DEVICE

BACKGROUND

Field

The subject described herein, in general, relates to an oral care device. More particularly, but not exclusively, the subject matter relates to detection of an oral condition and controlling operation of one or more cleaning elements.

Discussion of the Related Art

Oral health problems play a vital role in maintaining good health of an individual. Oral disorders like dental cavities, gingivitis and periodontitis are very painful and may cause irreparable damages to the individual, if not treated at proper time.

In general practice, the oral health of the individual remains unnoticed, until the user visits a dental practitioner. There may be a scenario, wherein an individual may not be aware of certain oral disorders that may be occurring in the oral cavity and fails to take required medical action in a timely manner, which may result in severe oral conditions and other health disorder. For example, severe periodontal disease if not diagnosed or treated at proper time, may result in tooth loss.

Detection of an oral condition using various dental devices operating independently are well known in the art. However, certain drawbacks are associated with the use of such devices. Typically, such devices are designed to be used in a lab under the observation of a medical practitioner. Further, such devices are hard to manoeuvre and therefore requires orienting the patient in specific ways to enable the medical practitioner to use such devices on the patient. Despite all these, the medical practitioners will still have to rely on their skills to determine how the oral health condition deteriorated to the current stage.

Further, on detection of certain oral condition, the dental practitioner may suggest health care actions to be taken by the individual. The dental practitioner may provide instructions for operating the toothbrush, dental floss or tongue cleaner in a certain way, and amount of pressure to be applied while performing the oral cleaning actions. It has been observed that despite such instructions provided, the individual fails to follow the regime as suggested. Secondly, there is also a need for the individual to visit the dental practitioner to determine, if the detected oral condition has been cured.

Attempts have been made to address certain problems, by using a partially automated cleaning devices such as an electronic toothbrush. Even these approaches fail to address certain drawbacks discussed above. Several studies have highlighted positive correlation of oral problems with other disorders, e.g., cardiovascular, respiratory, dementia, diabetes etc. Hence, good oral health is important not only for reduction of oral diseases but may also be crucial for improvement of overall health of the individual.

In light of the foregoing, there is a need of an improved oral care device that address the above drawback and enables automatic control of one or more cleaning elements based on detected oral condition.

SUMMARY

In one aspect an oral care device is disclosed. The oral care device comprises a head portion and a handle portion. The head portion comprises at least one supporting arm and a base. The supporting arm extends from the base. A sensor is exposed from the supporting arm. The handle portion is configured to move relative to the head portion. The handle portion comprises a processor, wherein the processor is configured to receive signals from the sensor and analyze the signals received from the sensor.

BRIEF DESCRIPTION OF DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form part of the detailed description. The drawings show illustrations in accordance with example embodiments. These example embodiments are described in enough details to enable those skilled in the art to practice the present subject matter. However, it may be apparent to one with ordinary skill in the art that the present invention may be practised without these specific details. In other instances, well-known methods, procedures and components have not been described in detail so as not to unnecessarily obscure aspects of the embodiments. The embodiments can be combined, other embodiments can be utilized, or structural and logical changes can be made without departing from the scope of the invention. The following detailed description is, therefore, not to be taken as a limiting sense.

In this document, the terms "a" or "an" are used, as is common in patent documents, to include one or more than one. In this document, the term "or" is used to refer to a non-exclusive "or", such that "A or B" includes "A but not B", "B but not A", and "A and B", unless otherwise indicated.

Figure 1A:
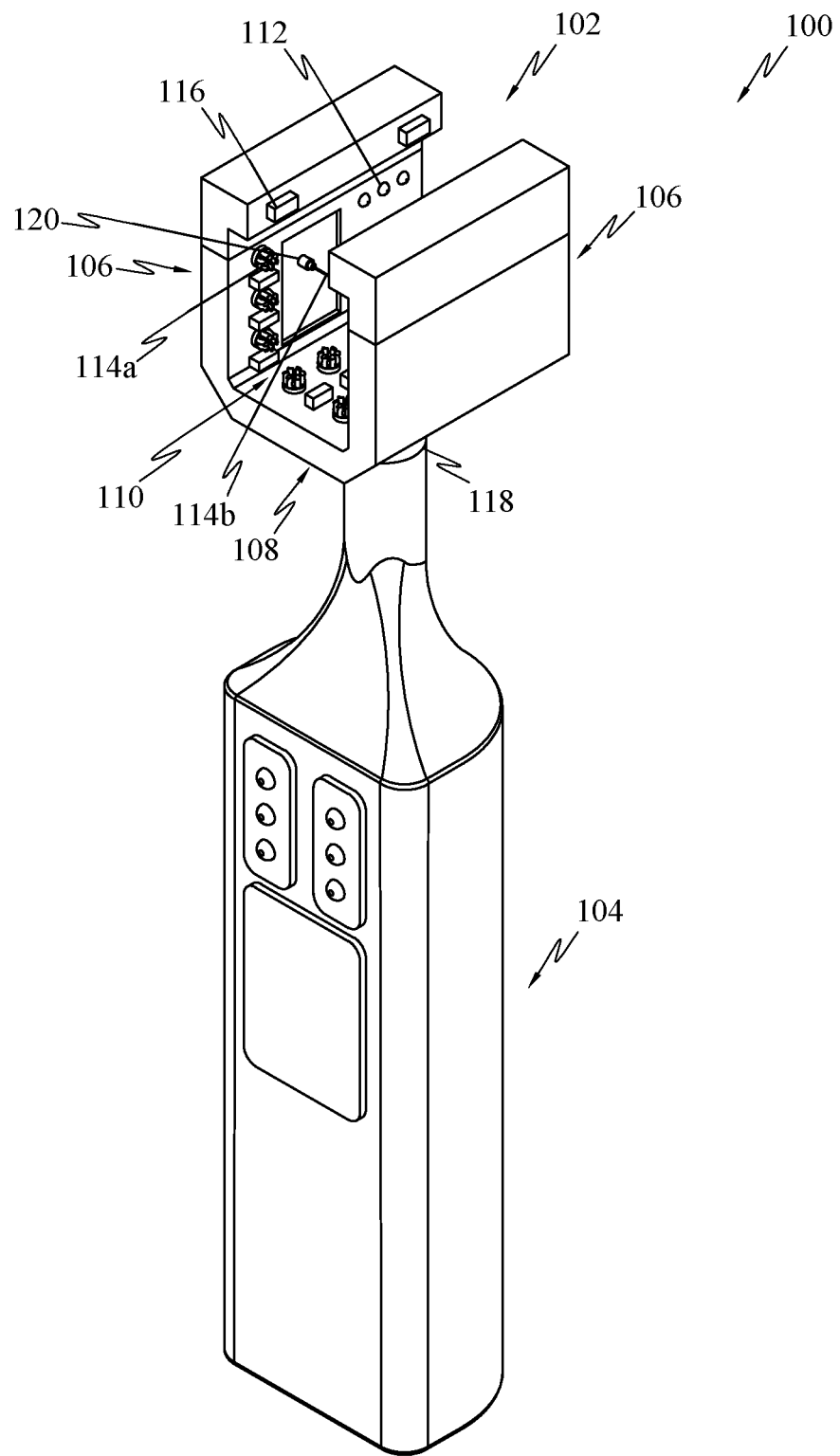
FIG. 1A illustrates an oral care device 100, in accordance to an embodiment.

We begin by referring to FIG. 1A, which illustrates an oral care device 100. The oral care device 100 comprises a head portion 102 and a handle portion 104. The head portion 102 of the oral care device 100 comprises a pair of supporting arms 106 and a base 108. Each of the supporting arms 106 extend from the base 108 defining a groove 110. The head portion 102 comprises one or more sensors 112 and one or more cleaning elements 114.

Figure 2A:
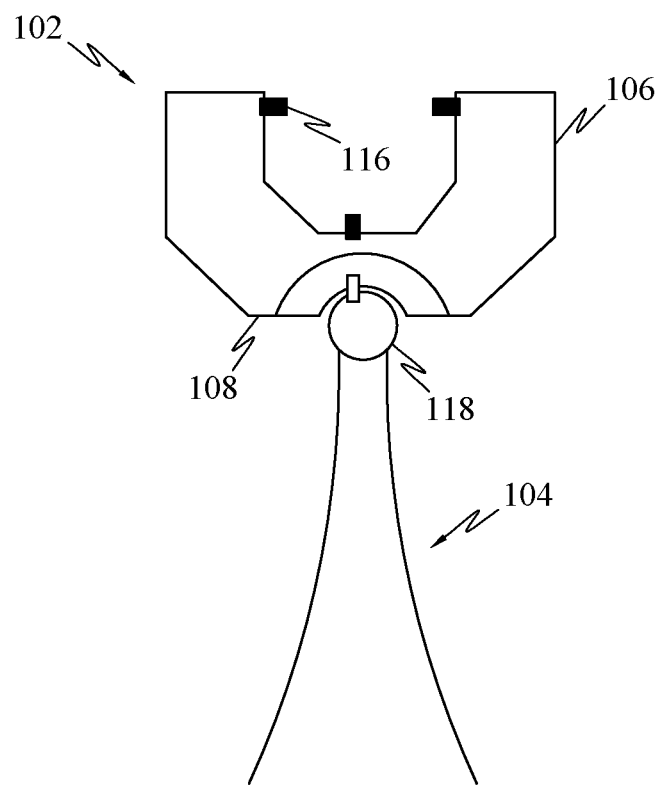
FIG. 2A illustrates a "U" shaped configuration of the head portion 102, in accordance with an embodiment.

FIGS. 2A-2G shows various possible configuration of the head portion 102 of the oral care device 100. In FIG. 2A, the head portion 102 has a U—shape configuration. The supporting arms 106 extending from the base 108 are parallel to each other. The edges of each of the supporting arms 106, which are in contact with the base 108 are curved or arc shape, defining smooth transition or transition that has edges.

Figure 2B:
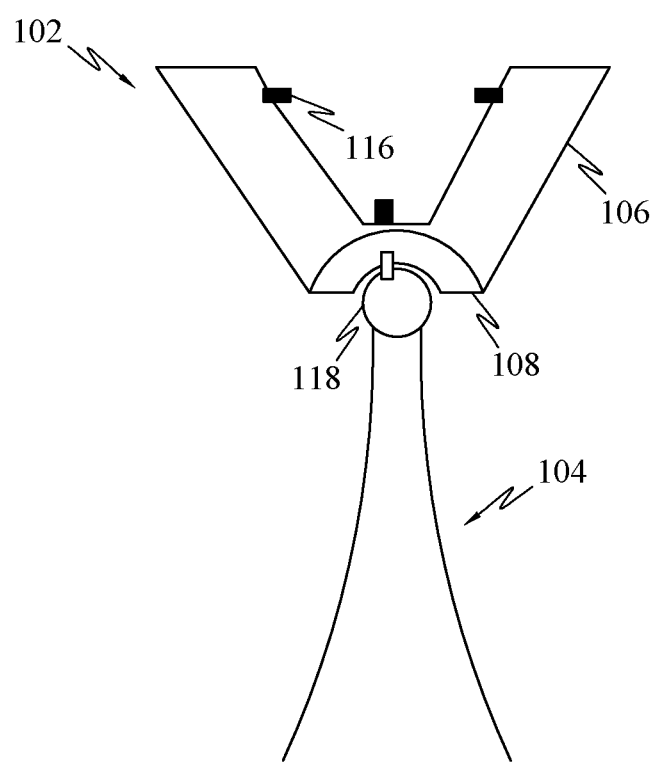
FIG. 2B illustrates a "V" shaped configuration of the head portion 102, in accordance with an embodiment.

In another embodiment, referring to FIG. 2B, the head portion 102 has a V-shape structure, wherein the each of the supporting arms 106 extending from the base 108 move away from each other forming a V-shape structure.

Figure 2C:
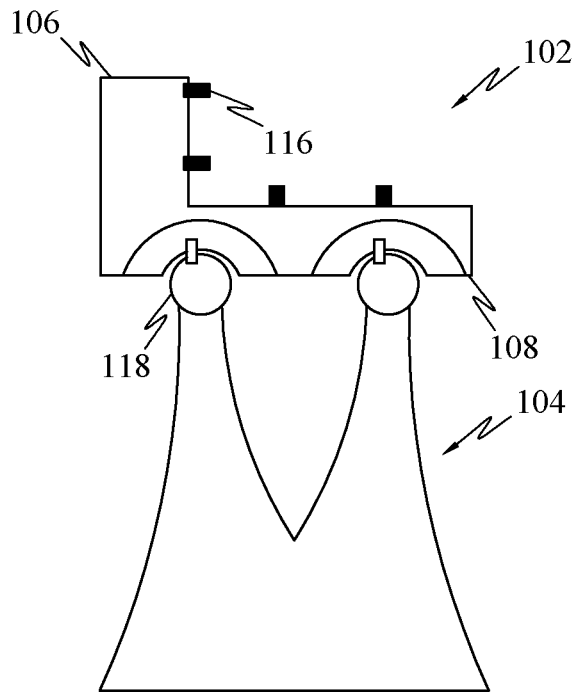
FIG. 2C illustrates a "L" shaped configuration of the head portion 102, in accordance with an embodiment.

In an alternate embodiment, referring to FIG. 2C, the head portion 102 comprises a single or only one supporting arm 106 extending from the base 108. In FIG. 2C the supporting arm 106 extends vertically from the base 108 such that the supporting arm 106 is generally perpendicular to the base 108 forming a L-shape structure.

Figure 2D:
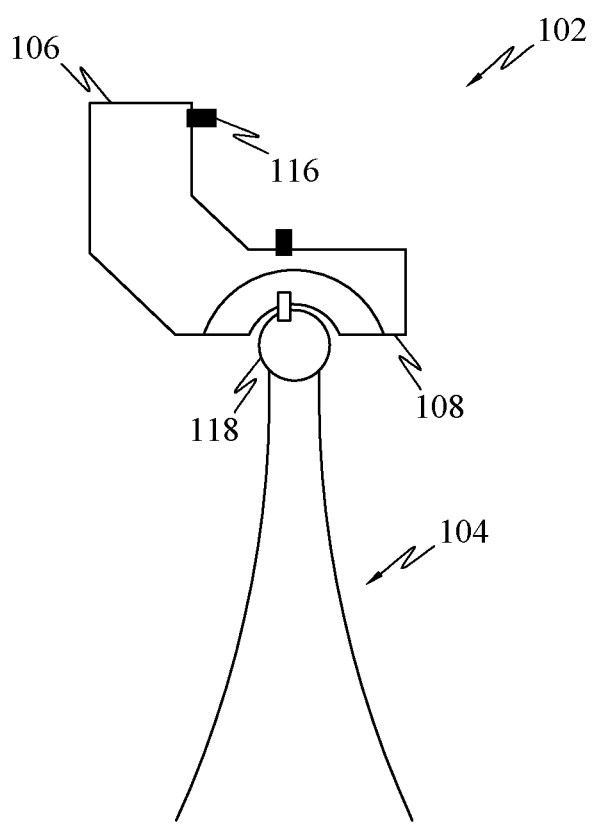
FIG. 2D illustrates an alternate "L" shaped configuration of the head portion 102, in accordance with an embodiment.

In FIG. 2D, the supporting arm 106 is curved at the edge joining or in contact with the base 108.

Figure 2E:
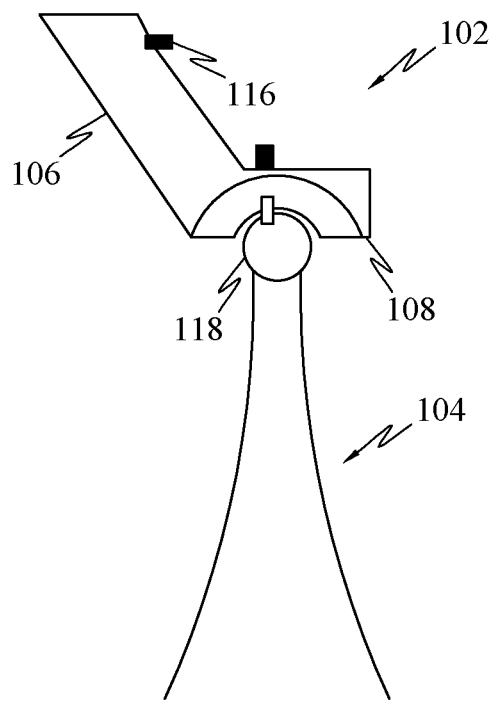
FIG. 2E illustrates yet another alternate "L" shaped configuration of the head portion 102, in accordance with an embodiment.

In FIG. 2E, the supporting arm 106 extend from the base 108 forming an angle oblique to the base 108.

Figure 2F:
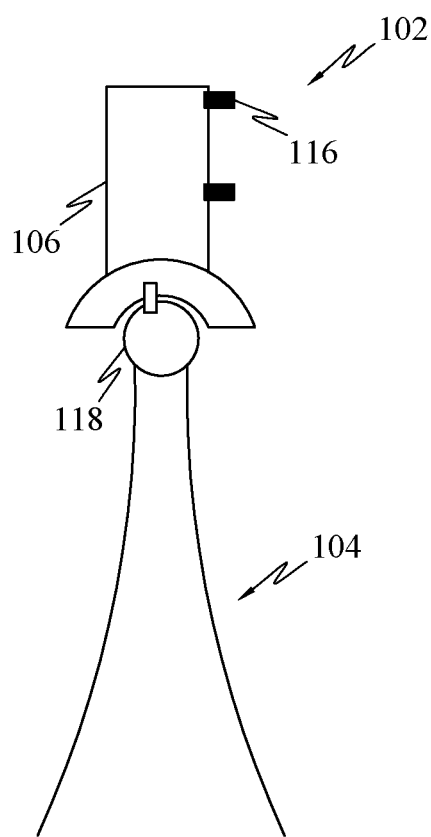
FIG. 2F illustrates a supporting arm 106 directly connected to a movement mechanism 118, in accordance with an embodiment.

In FIG. 2F, the supporting arm 106 is connected to a movement mechanism 118.

Figure 2G:
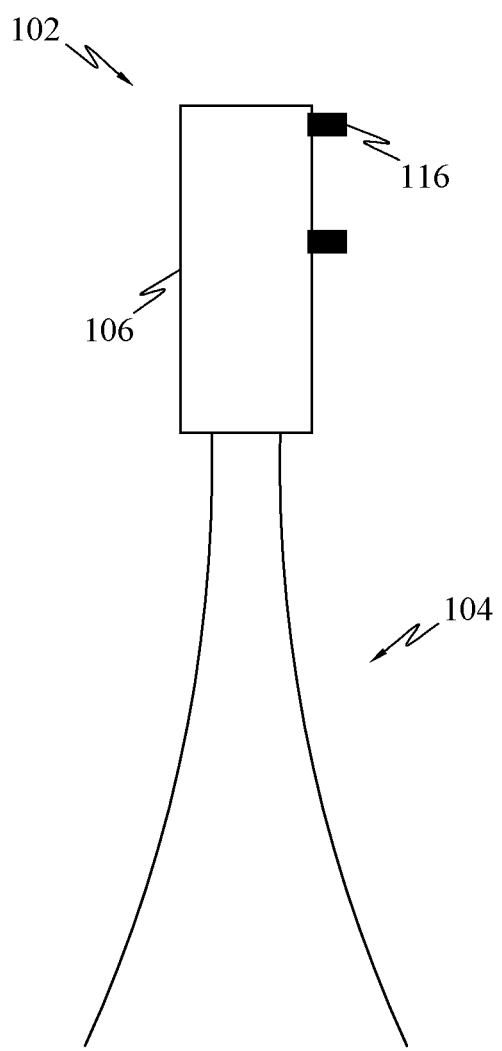
FIG. 2G illustrates the supporting arm 106 rigidly connected to a handle portion 104, in accordance with an embodiment.

In FIG. 2G, the supporting arm 106 is rigidly connected to the handle portion 104. Therefore, relative movement between the head portion 102 and the handle portion 104 is absent.

Referring to FIG. 1A, the oral care device 100 comprises one or more sensors configured to enable detection of one or more health (e.g., oral) conditions of a user using the oral care device 100. The sensors 112 are provided in the head portion 102 of the oral device which are exposed from the supporting arms 106.

The sensors 112 for example include but are not limited to ultraviolet spectroscopic sensor, infrared spectroscopic sensor, visible spectroscopic sensor, radio frequency sensor, or bioelectrical impedance sensor, temperature sensor or a combination thereof. The sensors 112 can be any sensors that enables detection of the oral condition.

In an embodiment, referring to FIGS. 3A-3D as well, the sensors 112 comprises an electromagnetic or an electrical energy emitting source 112a and an electromagnetic or an electrical energy detector 112b (detector mechanism). The electromagnetic or the electrical energy emitting source 112a is configured to radiate electromagnetic or electrical energy to a tooth in an oral cavity. The example of electromagnetic or electrical energy radiated or emitted may include infrared rays, ultraviolet rays, visible rays, radio frequency waves or electrical current.

In an embodiment, the electromagnetic or the electrical energy detector 112b is configured to detect reflected electromagnetic or electrical energy from at least one tooth.

In an embodiment, the electromagnetic or the electrical energy detector 112b is configured to detect electromagnetic or electrical energy transilluminated from at least one tooth.

In an embodiment, the electromagnetic or the electrical energy detector 112b is configured to detect electromagnetic or electrical energy transmitted from at least one tooth.

In an embodiment, the sensor 112 may comprise plurality of positive electrodes and plurality of negative electrodes, if the sensor 112 is a bioelectrical impedance sensor.

In an embodiment, the sensor 112 may comprise an RF transmitter and an RF receiver if the sensor 112 is an RF sensor. In this embodiment, the RF waves interact interface with the tooth or other body part to enable detection of an oral condition or health condition of the user.

In an embodiment, the sensor 112 may be a motion sensor configured to enable detection of motion of the oral care device 100. The motion sensor may be configured to determine relative position of the head portion 102 inside the oral cavity or user's mouth.

In yet another embodiment, the sensor 112 may be a pressure sensor configured to enable detection of pressure applied by one or more of the cleaning elements 114 on the user's teeth.

Moving on to the cleaning elements 114, the head portion 102 may be provided with the cleaning elements 114. The cleaning elements 114 may include a plurality of set of bristles 114a and a dental floss 114b configured to clean the oral cavity of the user. The plurality of set of bristles 114a and the dental floss 114b are provided within the groove 110.

The set of bristles 114a may be provided along each of the supporting arms 106 and the base 108, such that the set of bristles 114a are exposed to the groove 110. One set of the bristles 114a may be adjacent to another set of bristles 114a, the sensor 112, or the dental floss 114b. The arrangement of the cleaning elements 114a, 114b and the sensor 112 within the groove 110 is not limited to the arrangement described above or disclosed in the figures, however the arrangement may be in various ways that enables to achieve the objective of this disclosure.

In order to clean the food stuck, plaque formation or other undesired material in between the teeth, the region which cannot be reached by the set of bristles 114a, the dental floss 114b of the oral care device 100 is used. Each end of the dental floss 114b is engaged to a holding component 120, which is further engaged to the supporting arms 106 such that at least a portion of the holding component 120 is projected into the groove 110.

Figure 4A:
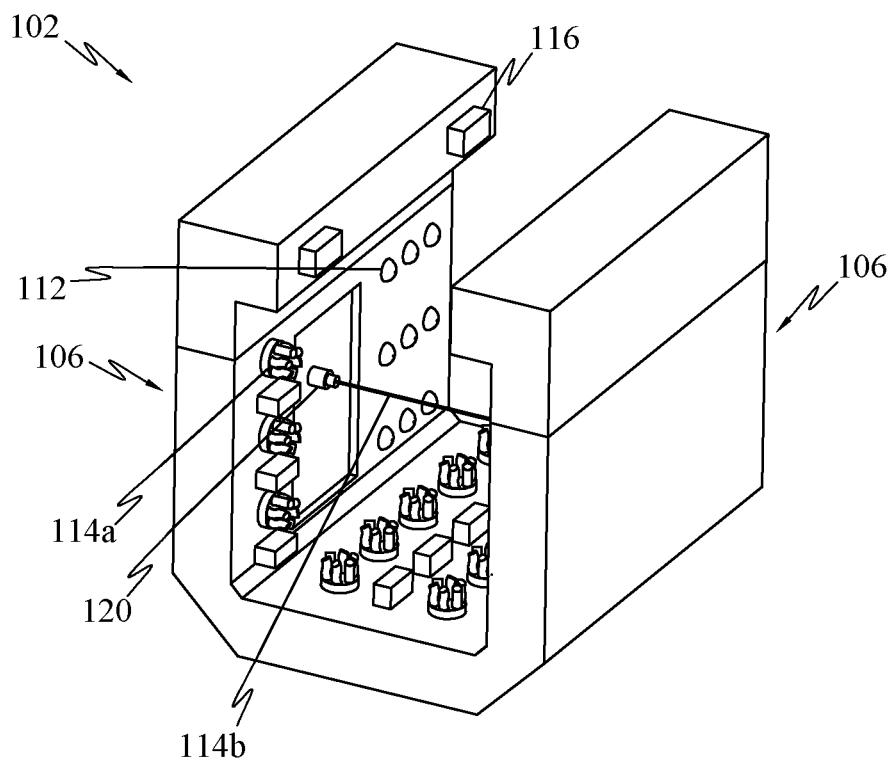
FIGS. 4A-4B illustrate movement of the dental floss 114b, in accordance to an embodiment.
Figure 4B:
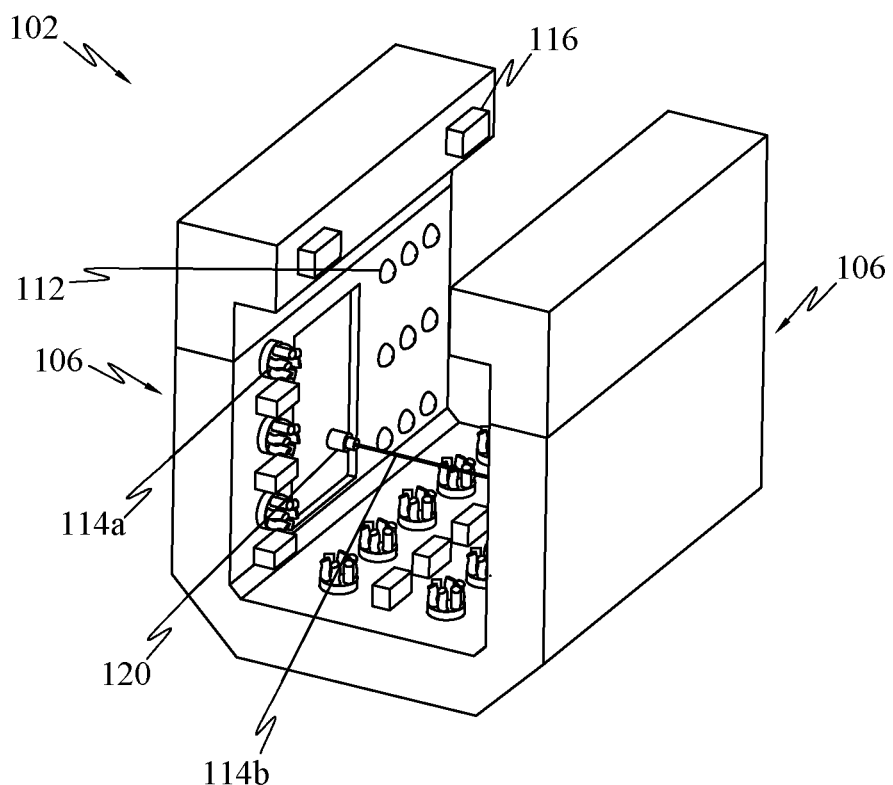

Referring to FIGS. 4A-4B, movement of the dental floss 114b is illustrated, in accordance to an embodiment. The dental floss 114b may be configured to move vertically along the supporting arms 106. In addition to the vertical movement, the dental floss 114b is may also be configured to move laterally, generally perpendicular to the vertical movement of the dental floss 114b. The movement of the dental floss 114b is actuated by a gear mechanism, a motor mechanism, a linear actuator mechanism or any mechanism (not shown) well known in the art which is embedded or accommodated within the holding component 120 and enables said movement of the dental floss 114b.

In an embodiment, the dental floss 114b is offset relative to the set of bristles 114a. The offset configuration of the dental floss 114b prevents the dental floss 114b from intersecting with the set of bristles 114b, when the dental floss 114b moves vertically or laterally.

The cleaning elements 114a and 114b, and sensors 112 may be arranged in various ways as seen in FIGS. 3A-3D. FIGS. 3A-3D illustrates a view of a side (tooth side) of a supporting arm 106, which faces the groove 110 (refer FIG. 1A).

Figure 3A:
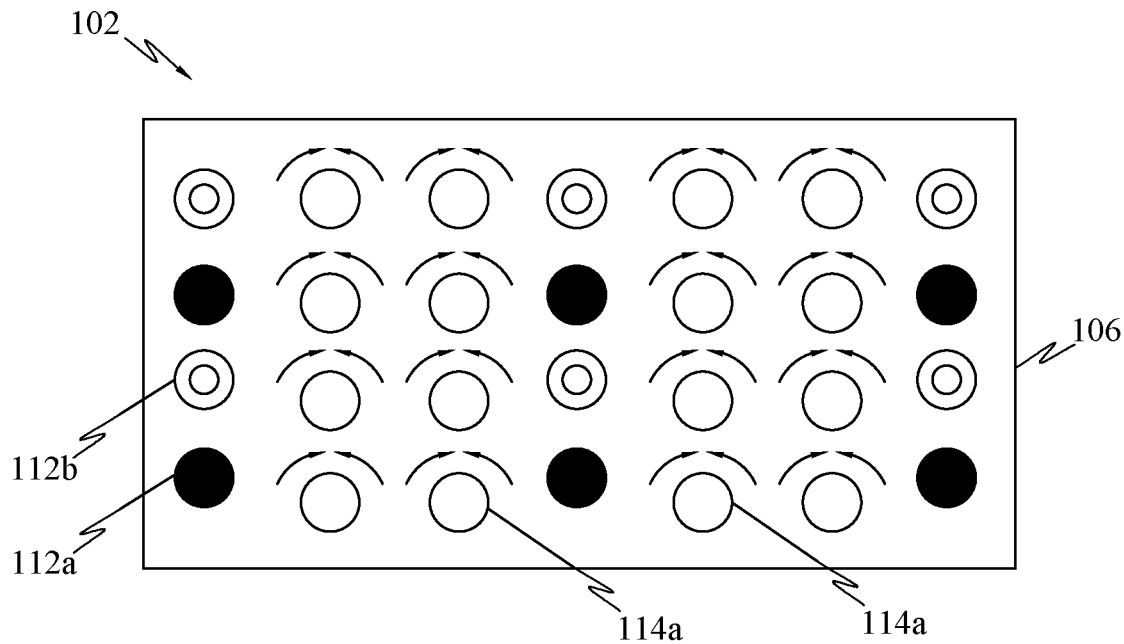
FIG. 3A illustrates a view of a side (tooth side) of a supporting arm 106, which faces the groove 110 (refer FIG. 1A), in which bristles 114a and sensor 112a and 112b are provided, in accordance with an embodiment.

In FIG. 3A, the electromagnetic or the electrical energy source 112a and the electromagnetic or the electrical energy detector 112b, and the set of bristles 114a are arranged vertically. The arrangement is such that in the first, fourth and seventh column the electromagnetic or the electrical energy source 112a and the electromagnetic or the electrical energy detector 112b are alternatively positioned in a vertical direction. In the second, third, fifth and sixth column, the set of plurality of bristles 114a are positioned vertically.

Figure 3B:
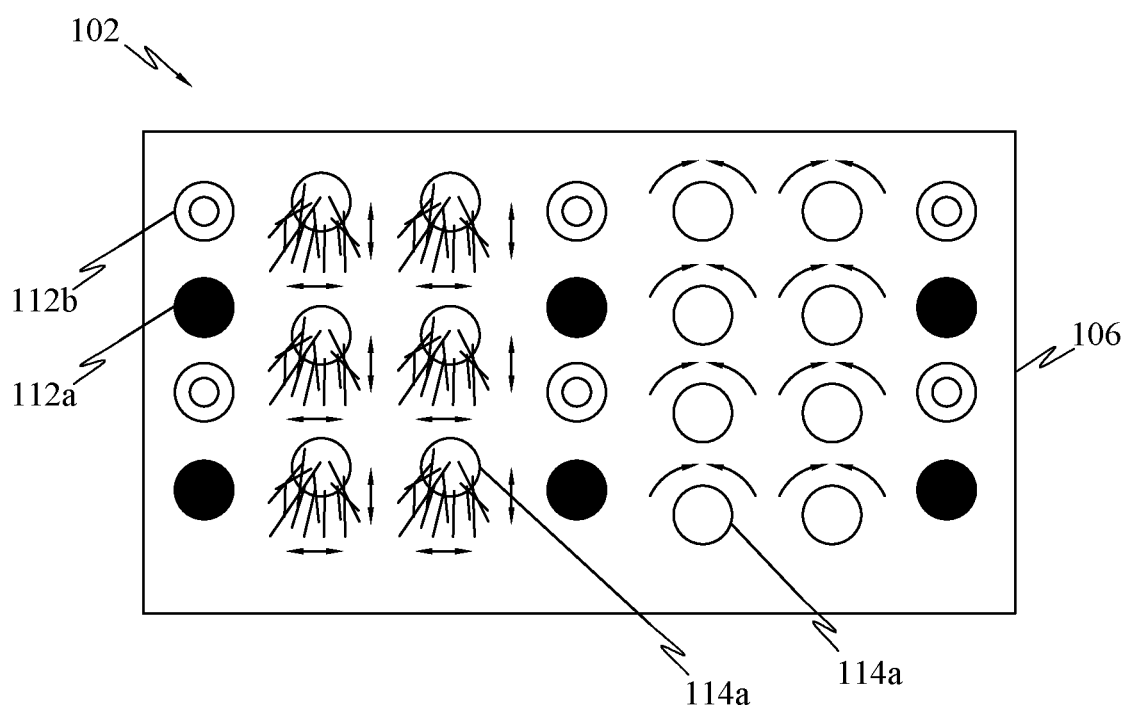
FIG. 3B illustrates the tooth side of a supporting arm 106 in which two types of bristles 114a are provided, in accordance with an embodiment.

FIG. 3B discloses a similar arrangement as seen in FIG. 3A, however design or structure of the set of bristles 114a positioned in the second and third column varies from the set of bristles 114a positioned in the fifth and sixth column. The bristles 114a in the second and the third column are configured to move linearly (e.g., vertical and lateral movement). The bristles 114a in the fifth and the sixth column are configured to move angularly (e.g., rotary movement).

Figure 3C:
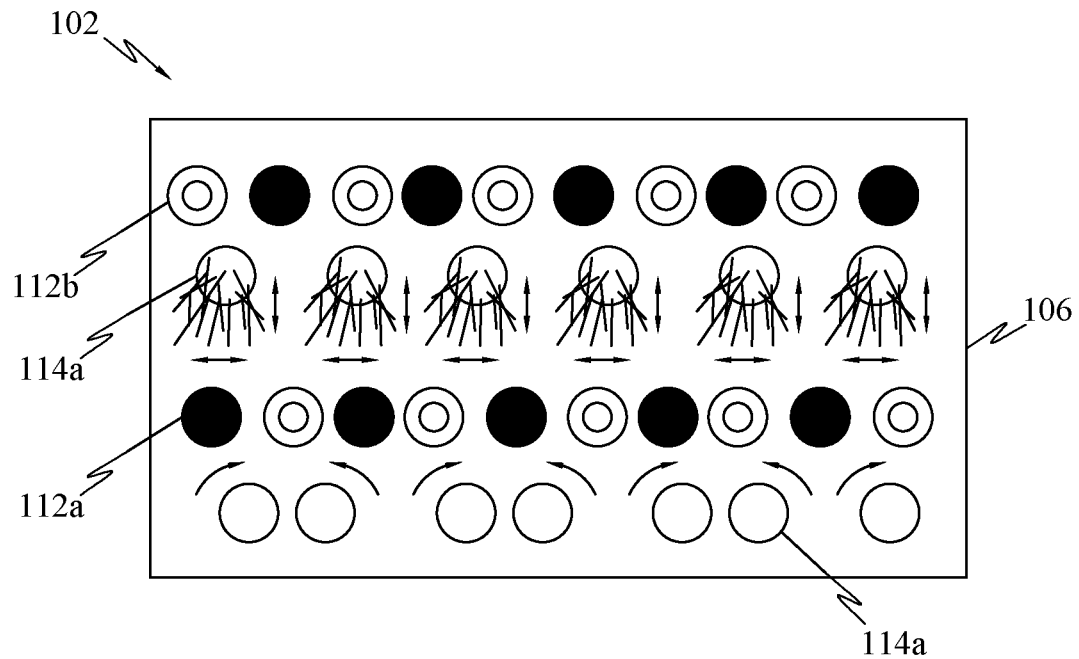
FIG. 3C illustrates the tooth side of a supporting arm 106 in which bristles 114a and the sensors 112a and 112b are arranged horizontally along the depth of the head portion 102, in accordance with an embodiment.

Referring to FIG. 3C, the electromagnetic or the electrical energy source 112a and the electromagnetic or the electrical energy detector 112b are arranged alternatively in horizontal direction in a first row and third row. The set of bristles 114a having a certain design is arranged horizontally in a third row and another set of bristles 114a having a different design is arranged in the fourth row.

Figure 3D:
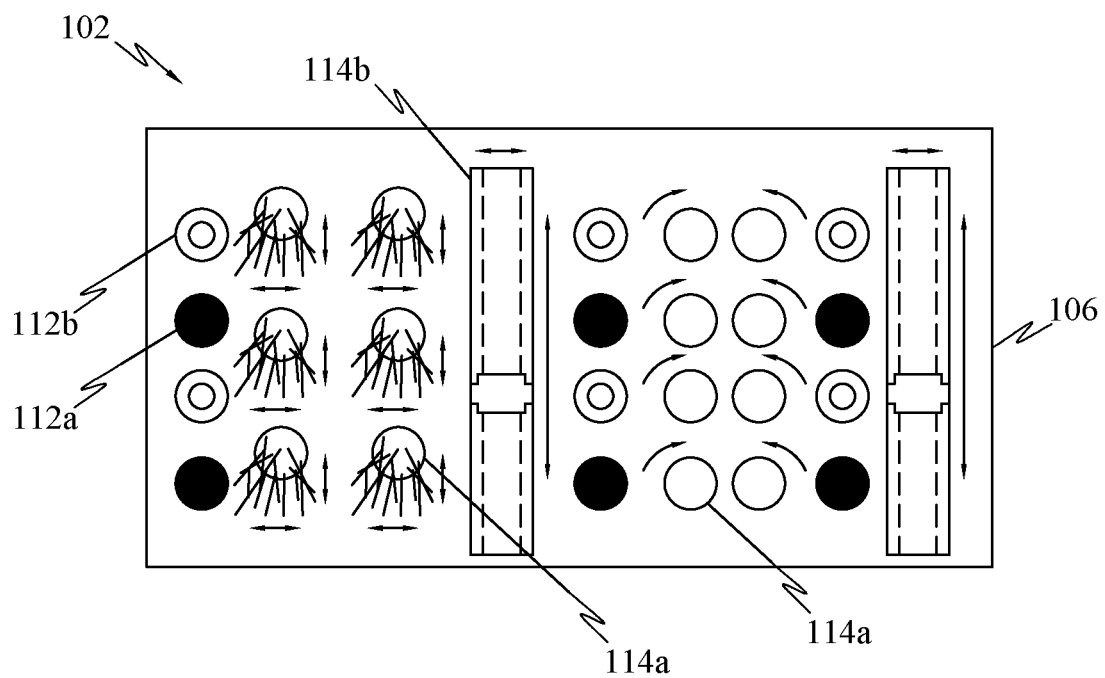
FIG. 3D illustrates the tooth side of a supporting arm 106 in which a dental floss 114b are provided, in accordance with an embodiment.

Referring to FIG. 3D, the electromagnetic or the electrical energy source 112a and the electromagnetic or the electrical energy detector 112b, are arranged alternatively in vertical direction. Even the set of bristles 114a, and the dental floss 114b are arranged vertically. One of the dental floss 114b is positioned in the fourth column and the second dental floss 114b is positioned in the ninth column. It shall be noted that the arrangements disclosed in FIGS. 3A-3D are just for illustrative purpose and not limited to arrangements disclosed in the figures.

Figure 1B:
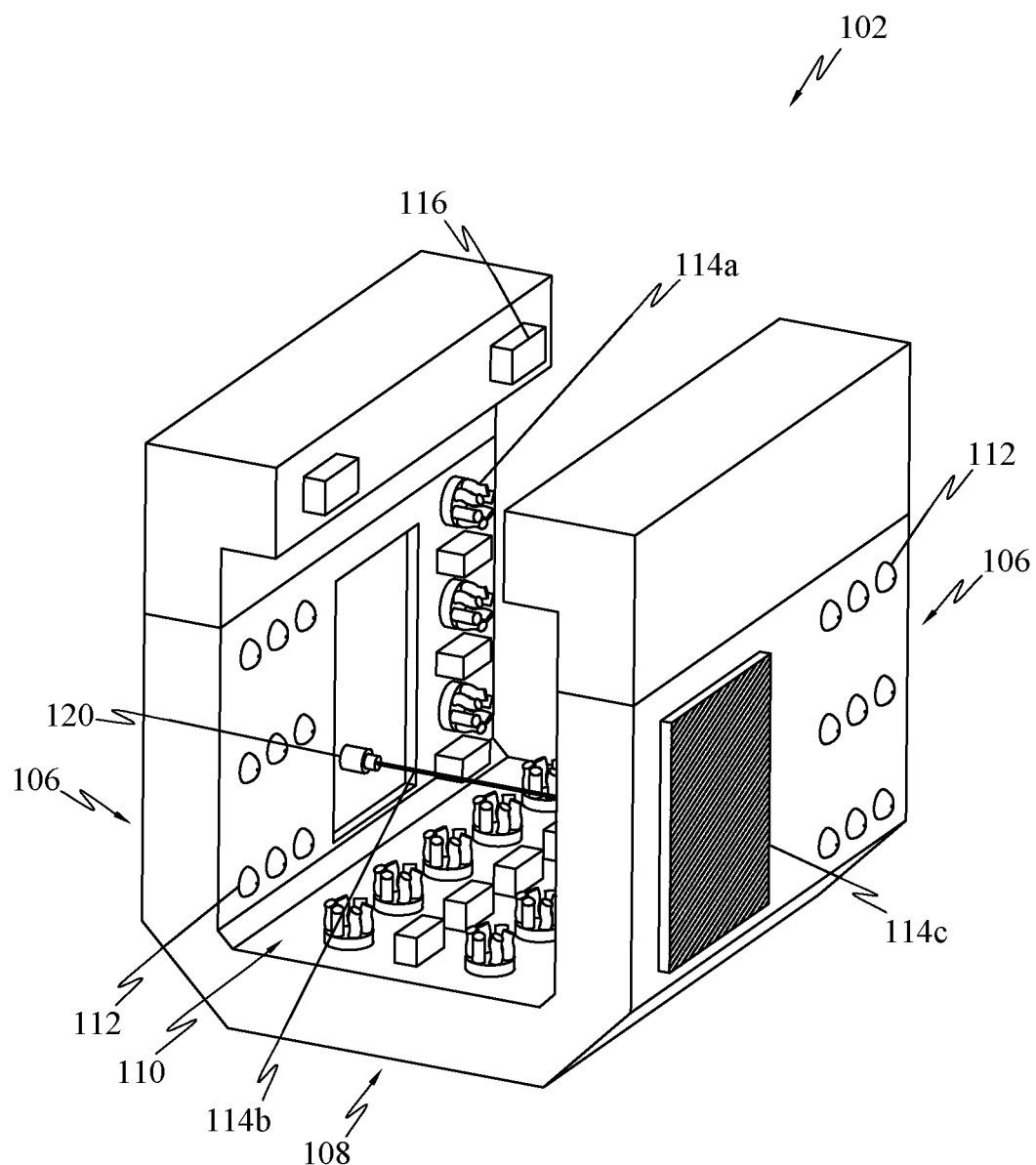
FIG. 1B illustrates another view of a head portion 102 of the oral care device 100 of FIG. 1A, in which a tongue cleaner 114c provided on the head portion 102 is visible, in accordance to an embodiment.

Referring to FIG. 1B the cleaning elements 114 further comprises a tongue cleaner 114c configured to remove coating that may be present on an upper surface of the tongue. The tongue cleaner 114c is provided on the head portion 102 of the oral care device 100. The tongue cleaner 114c is provided on one of the supporting arms 106 of the head portion 102 of the oral care device 100 and configured to move in a horizontal direction or vertical direction. More specifically, the tongue cleaner 114c is provided on a side opposite to the groove 110. Further, a movement of the tongue cleaner 114c may be based on the signal detected by the sensor 112.

The tongue cleaner 114c may be arranged in various possible ways on the head portion 102 of the oral care device 100 (refer FIG. 5A-5D). The tongue cleaner 114c may have different patterns defined by embossed textures. Further, the set of bristles 114a are also configured to clean the surface of the tongue similar to the tongue cleaner 114c.

Figure 5A:
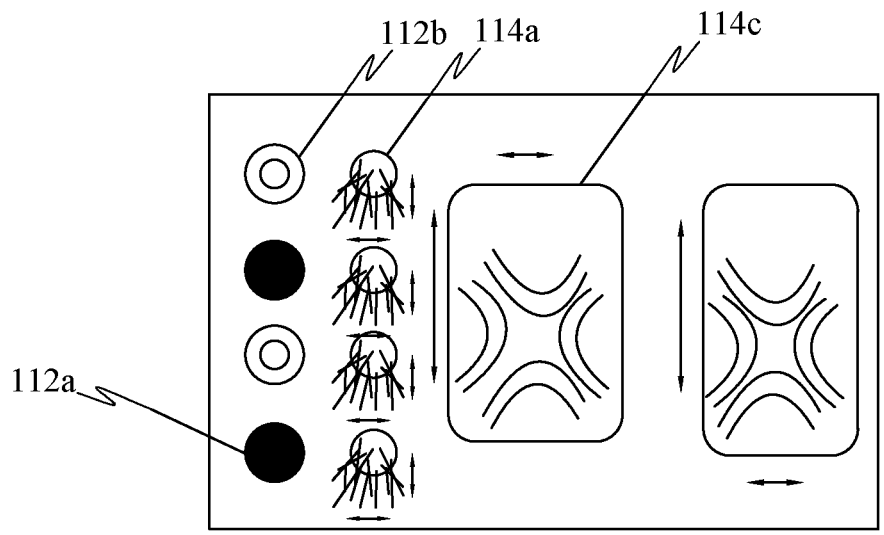
FIG. 5A illustrates a view of a side (outside) of a supporting arm 106, which faces away from the groove 110 (refer FIG. 1A), in which a pair of movable tongue cleaners 114c are provided, in accordance with an embodiment.
Figure 5B:
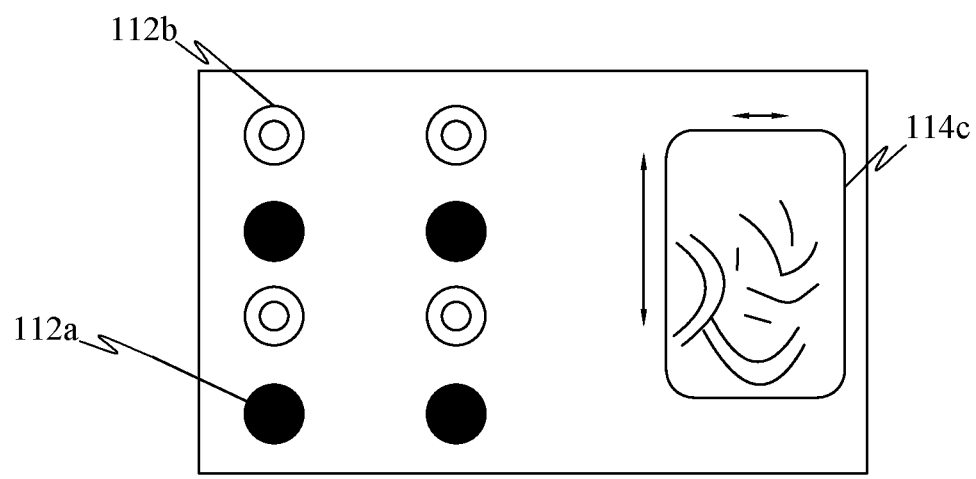
FIG. 5B illustrates a view of an outside view of a supporting arm 106 in which a single movable tongue cleaner 114c is provided, in accordance with an embodiment.
Figure 5C:
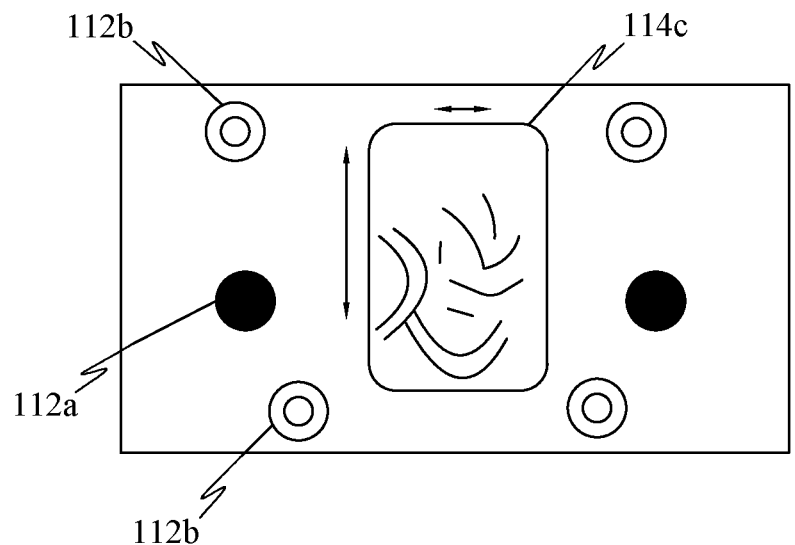
FIG. 5C illustrates a view of an outside view of a supporting arm 106 in which a single movable tongue cleaner 114c is provided, in accordance with an embodiment.
Figure 5D:
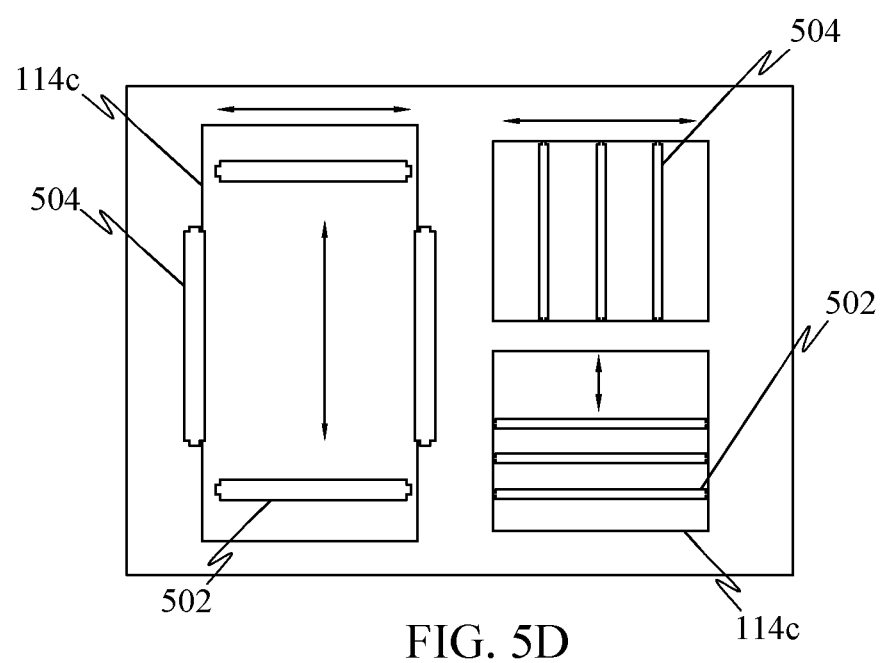
FIG. 5D illustrates a view of an outside view of a supporting arm 106 in which a three tongue cleaner 114c with movable cleaning strips 502 and 504 are provided, in accordance with an embodiment.

In an alternate embodiment, the head portion 102 of the oral care device 100 comprises more than one tongue cleaner 114c as shown in FIGS. 5D and 5A.

Now referring to FIG. 5D, the head portion 102 comprises at least three tongue cleaner 114c. One of the tongue cleaner 114c comprise one or more horizontally moving strips element 504 that can clean the tongue with the movement of said one or more strips. The second tongue cleaner 114c comprises one or more vertically moving strips element 502 that can clean the tongue with the movement of the one or more strips across length or height of the supporting arms 106 or the head portion 102. The third tongue cleaner 114c comprises moving strips elements comprising one or more vertically moving strips 502 and one or more horizontally moving strips 504 that enable the cleaning of the tongue with the movement of the vertically moving strips 502 along the height of the supporting arms 106 or the head portion 102 and movement of the horizontally moving strips 504 along the breadth/depth of the supporting arms 106 or the head portion 102. It shall be noted that the set of bristles 114a, the dental floss 114b and the tongue cleaner 114c may be collectively referred as the cleaning elements 114.

Now referring to FIGS. 1A and 1B, the oral care device 100 further comprises spacer components 116. The spacer components 116 provided on the head portion 102 of the oral care device 100 project into the groove 110. The spacer components 116 are configured to prevent the tooth from rubbing against a portion of the sensor 112 which is exposed towards the teeth. The spacer components 116 may be provided on each of the supporting arms 106 and the base 108, wherein at least a portion of the space components 116 project into the groove 110. Further, the spacer components 116 may be provided only on the supporting arms 106 or the base 108.

The spacer components 116 projecting from the supporting arms 106 are dimensioned to regulate pressure applied by one or more of the cleaning elements 114 over one or more tooth of the user, regulate distance of one or more of the cleaning elements 114 from the user's teeth or to position the sensor 112 at a distance from the user's teeth. The distance of the sensor 112 from the teeth may be decided based on the distance desired for proper functioning of the sensor 112.

The spacer components 116 are further configured to assist in proper operation of the sensors 112 or the cleaning elements 114. Secondly, the spacer components 116 also help to protect the exposed components and elements from expedited wearing as a result of repeated and accidental contacts with sharp or rough or other surfaces.

In an embodiment, the spacer component 116 is positioned to interface with the gum of the user.

In an embodiment, at least some of the spacer component 116 are manufactured using materials, such as, but not limited to, piezoelectric material i.e. material that helps to sense exerted pressure, and elastomers defined as materials with variable or controllable stiffness, among others.

In an embodiment, the head portion 102 is mounted to the handle portion 104 by a joint that enables fixed mounting of the head portion 102 to the handle portion 104.

In another embodiment, the head portion 102 is pivotably mounted on the handle portion 104 by a mounting, wherein the mounting may be a pivotable connection or movable connection 118 (movement mechanism) for the movement of the head portion 102 relative to the handle portion 104. The pivotable connection 118 is engaged or connected to a tip portion of the handle portion 104 at one end and to the base 108 on the other end. Further, the pivotable connection 118 enabling the pivotable mounting of the head portion 102 to the handle portion 108 is for example but not limited to a ball joint connection, cylindrical joint or any joint or element that enables the pivotable mounting of the head portion 102 relative to the handle portion 104. The oral care device 100 may comprise more than one pivotable connection 118. (shown in FIG. 2C).

Figure 6:
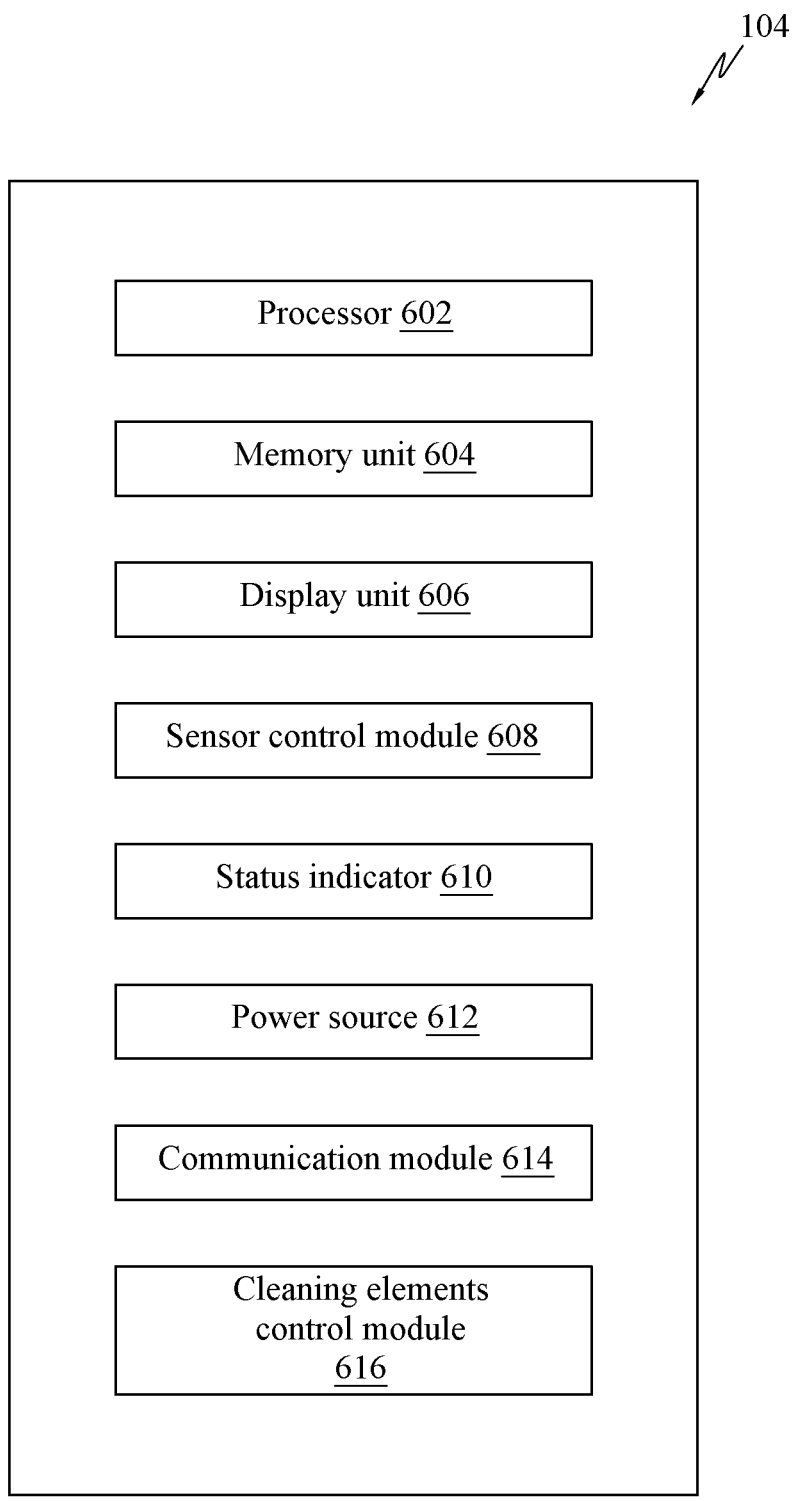
FIG. 6 illustrates a schematic block diagram of a handle portion 104 of the oral care device 100, in accordance to an embodiment.

In the foregoing description, the head portion 102, the cleaning elements 114a, 114b 114c, and the pivotable connection 118 were discussed in detail. We now move on to discussing the various components provided in the handle portion 104. FIG. 6 is a schematic block diagram of the handle portion 104. The handle portion 104 comprises a processor 602, a memory unit 604, a display unit or user interface 606, sensor control elements 608, a status indicator 610, a power source 612, a communication module 614 and a cleaning elements control module 616. The memory unit 604 may include a permanent memory such as hard disk drive, may be configured to store data, and executable program instructions that are implemented by the processor. The memory unit 604 may be implemented in the form of a primary and a secondary memory. The memory unit 604 may store additional data and program instructions that are loadable and executable on the processor, as well as data generated during the execution of these programs. Further, the memory unit 604 may be a volatile memory, such as a dynamic random-access memory or anon-volatile memory such as disk drive. The memory unit 604 may further comprise of removable memory such as a Compact Flash card, Memory Stick, Smart Media, Multimedia Card, Secure Digital memory, or any other memory storage that exists currently or may exist in the future.

The processor 602 may be a microprocessor or microcontroller, as an example. The processor 602 is configured to receive signals from the sensor 112. The term signal includes an optical signal, an electrical signal, any other signal or data. Cable may be configured to connect the sensor 112 to the processor 602 enabling signal transmission to the processor 602. The processor 602 is further configured to analyse the signals received from the sensor 112. On analysis of one of the signals received from the sensor 112, the processor 602 is configured to determine at least one oral condition, a health condition or both. The cable also connects one or more of the cleaning elements 114 to the processor 602.

The signals analysed by the processor 602 may be pre-processed using pre-processing techniques to improve signal to noise ratio of the signal detected by the sensor 112. The pre-processing techniques are for example but not limited to noise filtering, and signal enhancement, among other techniques that are well known in the art.

The oral device 100 is configured to identify symptoms relating to certain disorders by analysing using the processor 602, the pre-processed signals or raw signals received from the sensors 112. The disorders identified or determined are for example but not limited to inflammation in a gum, tooth structure or gum shape deformities, abnormal vitamin levels, abnormal hormone levels, abnormal body cell or tissues, presence of pathogens, plaque, tartar, food particles, by products of pathogen activities and abnormal tooth surface color. The oral care device 100 may also configured to determine plaque, gingivitis, tooth cavity (dental caries) formation, tooth demineralization periodontitis, halitosis, hormonal problems, vitamin and mineral deficiencies, improper oral hygiene, tumour, or cancer among others.

On detection of the at least one health or oral health condition, the processor 602 is configured to determine one or actions to be performed using the oral care device 100, for example cleaning of the teeth and oral cavity, treating the detected condition using the IR, UV or RF energy or combination thereof. The processor 602 is also configured to control operation of at least one of the cleaning elements i.e. the set of bristles 114a, the dental floss 114b and the tongue cleaner 114c based on the analysed signals. For example, if improper oral hygiene is detected then the processor 602 determines that operation of the set of the bristles 114a is required to clean a specific tooth area in a highly selective and precise manner for a predetermined time. An actuator may be provided in the oral care device 100, which is controlled by the processor 602. The actuator is configured to operate at least one of the cleaning elements 114a, 114b, and 114c. The actuator may be for example but not limited to a rotary actuator, or a linear actuator among other types of actuator known in the art. In another embodiment, the actuator may be an electric motor.

The processor 602 is also configured to analyse the data received from the pressure sensor and thereby control the operation of one of the cleaning elements 114, if the pressure applied exceeds or lower than predefined set of threshold values.

The oral care device 100 may be configured to perform adaptive cleaning of various parts of the oral cavity based on their cleanliness condition, detected and diagnosed disorders, and specific nature of foreign material. The oral care device 100 may detect the nature of food, drinks and smoke consumed by the user, and determine that extensive and prolonged cleaning is required, and accordingly controls the functioning of the cleaning elements. Alternatively, the oral care device 100 may detect that the oral cavity is free of harmful materials or pathogens. Based on the detection the oral care device 100 determines that relatively softer or less aggressive cleaning is required, and accordingly controls the functioning of the cleaning elements 114. In essence, oral care device 100 enables determination of the effective cleaning regime based on the oral health condition.

Figure 7A:
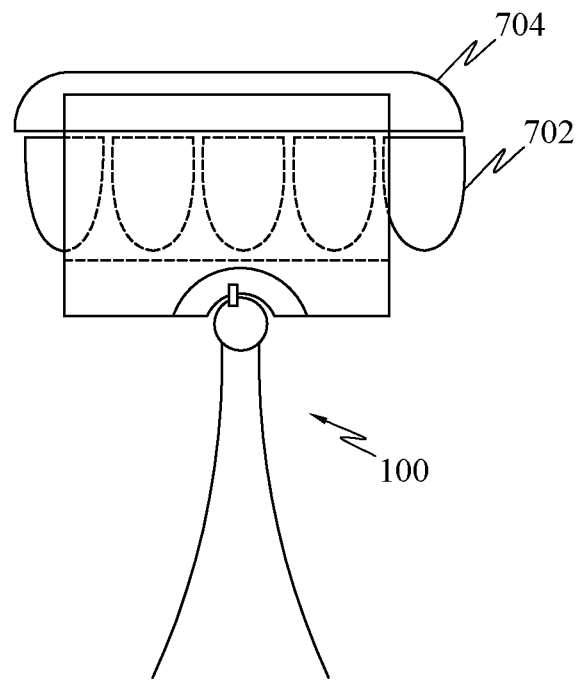
FIG. 7A illustrates the oral care device 100 interfacing with the teeth 702 of a user, in accordance to an embodiment.
Figure 7B:
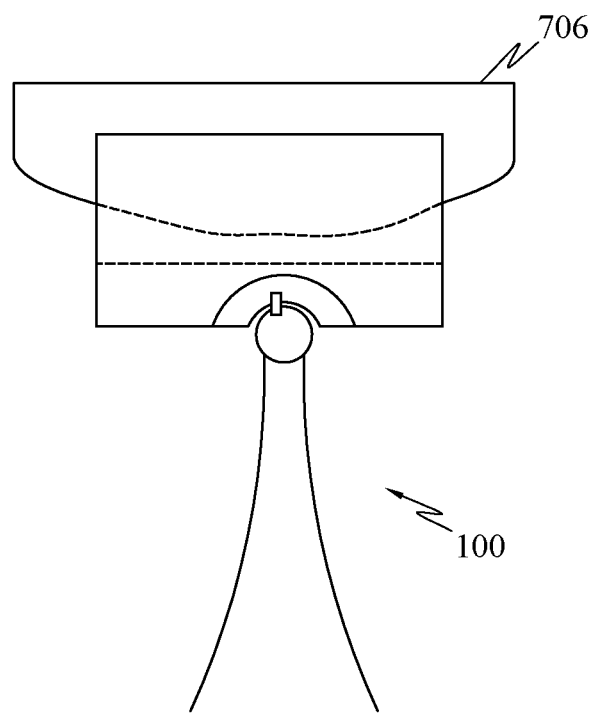
FIG. 7B illustrates the oral care device 100 interfacing with the tongue 706 of a user, in accordance to an embodiment.

FIG. 7A illustrates the oral care device 100 interfacing with the teeth 702 and gum 704 of the user, in accordance to an embodiment. FIG. 7B illustrates the oral care device 100 interfacing with the tongue 706 of the user, in accordance to an embodiment.

Further, the spacers 116 may be made movable with their movement controlled by the processor 602 of the oral care device 100 for various reasons, for example but not limited to avoid inconvenience to the user by automatically bringing applied pressure in the desired range in various conditions.

In an embodiment, the signal analysed by the processor 602 of the oral care device 100 is displayed on the user interface 606 (display unit) provided on the handle portion 104 of the oral care device 100. Further, one or more actions to be performed by the oral care device 100 for the user may also be displayed on the user interface 606. The user interface 606 may be a display unit such as Liquid Crystal Displays (OLCD) or any other type of display currently existing or which may exist in the future that enables the display of the analysed signal, recommendations such as general physician consultation, cancer specialist consultation, endodontist consultation, general dentist consultation, and proper oral cavity cleaning techniques among others. For example, the information received by the user interface 606 can be read, viewed, heard, felt, and/or otherwise interpreted concerning various features or relevant aspect of this disclosure.

In yet another embodiment, the analysed signal from the processor 602 may be displayed using status indicators 610, for example but not limited to color light emitting diodes (LEDS). The status indicator 610 may also be configured to indicate the status of the power source 612. For example, the blinking of the red light may indicate that the battery of the oral care device 100 is low and the oral care device has to be charged. In yet another embodiment, LEDs may indicate detected, diagnosed, cleaned or corrected health status of the user.

The sensor control module 608 may include a part of the sensing elements while other parts may be housed in the head portion 102. The sensor control module 608 may control the operation of various sensors 112 provided in the oral care device 100.

The cleaning elements control module 616 may control the operations of one or more of the cleaning elements 114. The operation or function of the cleaning elements control module 616 is further controlled by the processor 602.

The power source 612 is provided in the handle portion 104 which is configured to provide electrical energy for the operation of the oral care device 100 and distribution of electrical energy to all the electrically powered components of the oral care device 100. Further, an electrical cable is configured to connect one or more of the cleaning elements 114 and the sensor 112 to the power source 612. The electric cable passes through the mounting and further connects to the power source 612.

The power source 612 may be a rechargeable battery, for example but not limited to rechargeable lithium-ion battery or a battery that is comprised of one or more electrochemical cells that convert stored chemical energy into electrical energy, which is then distributed to the remaining electrically powered components. Two primary types of batteries are utilized in some embodiments including disposable batteries and rechargeable batteries Some of the elements, or part of their functionality, discussed with reference to FIG. 6 may be incorporated into the head portion 102. Likewise, some of the functions of the sensors 112 may be incorporated into the handle portion 104.

Figure 8:
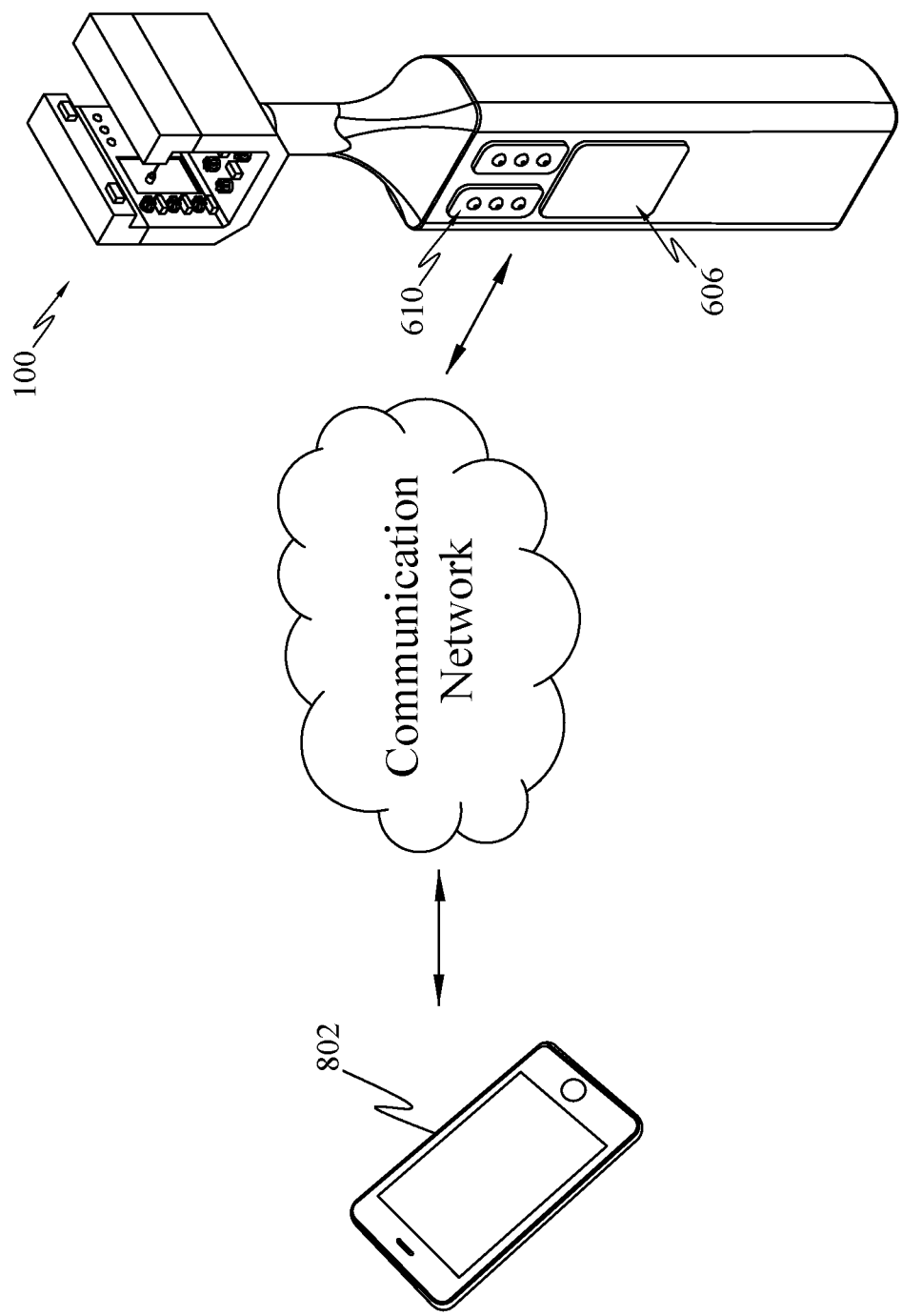
FIG. 8 illustrates communication of the oral care device 100 with an external device 800, in accordance to an embodiment.

Referring to FIG. 8 the oral care device 100 may be in communication with an external device 800. The communication module 614 enables wireless communication of the oral care device 100 with the external device 802 via a communication network. The communication module 614 may include devices supporting both wired and wireless protocols.

The external device 800 may be a remote device configured to receive and process the signals transmitted from the sensor 112. For example, the external device 800 may be a smartphone device, a computer, a tablet, a server, or any other computerized device. The external device 800 includes a processor, a communication module, a display unit (user interface) and a memory unit. The memory unit is configured to store received detected signal from the sensor 112, or any other information.

In an embodiment, the processor 602 of the oral care device 100 is configured to communicate information to the external device 800. The information communicated may be based on the analysis of the signals received from the sensor 112 or one or more of the cleaning elements 114.

In an embodiment, the signal detected by the sensor 112 of the oral care device 100 is processed by the processor of the external device 800. The processed and analysed data may be then transmitted to the processor 602 of the oral care device 100 so that the processor 602 of the oral care device 100 may control the operation of one of the cleaning elements 114. Alternatively, the operations of one of the cleaning elements 114a, 114b or 114c may be controlled by the processor of the external device 800.

In an embodiment, the analysed signal and recommendations are transmitted to the external device 800 and further displayed on a user interface of the external device 800. The external device 800 may be a standalone device comprising a display unit to display the analysed signals and recommendations from the oral care device 100 or any data from the oral care device 100.

In an embodiment, an automatic toothpaste dispenser unit may be coupled to the oral care device 100.

In an embodiment, an automatic dental floss dispenser unit may be coupled to the oral care device 100.

In an embodiment, the oral care device 100 may send an alert signal to the user, if the sensed parameter for the movement of the handle portion 104 exceeds or fall below the predefined parameters.

Further, the oral care device 100 is configured to notify or alert the user about the wear and tear condition of the various components of the oral care device 100. For example, if any of the components such as the cleaning elements 114a, 114b and 114c are in a condition that can no longer assist in effective cleaning or the sensor 112 is incapable to perform its desired function, the oral device 100 is configured to send such notification to the user.

Figure 9:
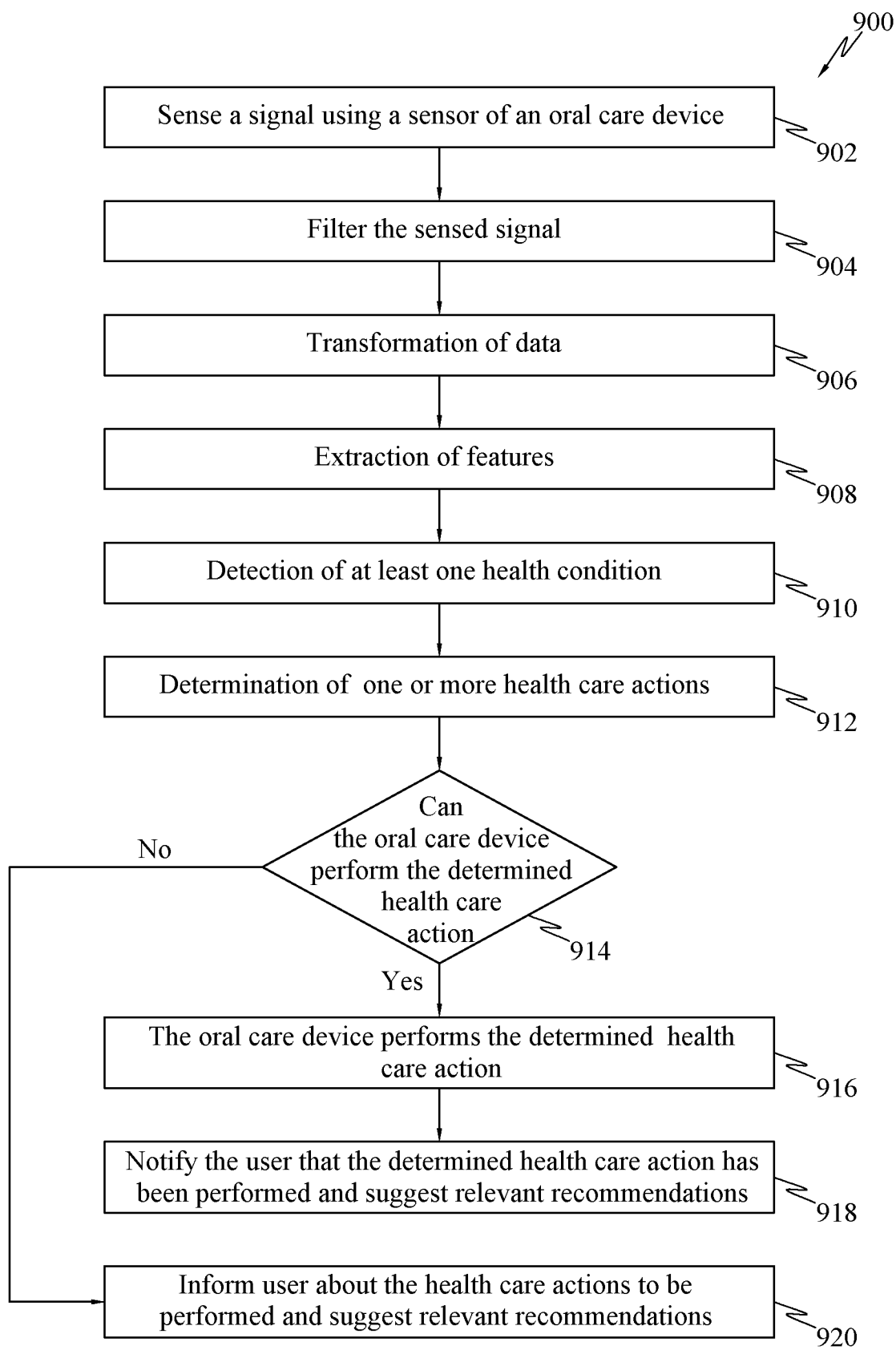
FIG. 9 is an exemplary method flowchart for detection of at least one health condition using the oral care device 100 in accordance to an embodiment.

FIG. 9 is an exemplary method flowchart for detection of at least one health condition using the oral care device 100. At step 902, the sensor 112 of the oral care device 100 enables detection of at least one health condition by sensing signals from the tooth. The term signal includes an optical signal, an electrical signal, any other signal or data. The signals detected by the sensor 112 are pre-processed using pre-processing techniques to improve signal to noise ratio resulting in signal enhancement (at step 904).

At step 906, the data received from the step 904 is transformed into structure or values such that the transformed data is suitable for further analysis. The data transformation techniques are for example but not limited to Fourier transform, Hilbert transform, logarithmic transform, Wavelet Decomposition, and Empirical Mode Decomposition among others.

At Step 908, the data received from the step 906 is further processed to create a data set with potentially reduced number of variables, which include the most discriminatory information (feature extraction). The feature extraction technique may be for example but not limited to Principal Component Analysis, Independent Component Analysis, and Autoencoder among others.

At step 910, the processor 602 of the oral care device 100 is configured to use the extracted features to detect the health condition of the user. For example, but not limited to, cavity formation in the tooth, abnormal blood sugar levels, inflammation in the gum, gum bleeding, abnormal vitamin levels, teeth demineralization, halitosis, cancer, gum disorders, infection, and abnormal body cells and tissues among others.

Based on the detection of the health condition of the user (at step 910), the oral care device 100 is also configured to determine one or more health care actions (at step 912). The health care actions may include, cleaning the tooth or the oral cavity, and cleaning the tooth more frequently in the area close to the user's gum in case of gum bleeding among others.

At step 914, the oral care device 100 determines, if the determined health care action can be performed by the device 100. If the health care action can be performed by the oral care device 100, at step 916 the oral care device 100 is configured to perform said health action. For example, cleaning of the tooth and oral cavity and treatment of infections detected using infrared, ultraviolet, radiofrequency energy or combination thereof. The user is further notified about the completion of the determined health care action to be performed at step 918. The notification may be displayed in the display unit 606 of the oral care device 100, or on the display unit of the external device 800. Additionally, the oral care device 100 is also configured to provide relevant recommendations to the user at step 918. For example, but not limited to, general physician consultation, cancer specialist consultation, endodontist consultation, and general dentist consultation, among others. This information is displayed on the display unit 606 of the oral care device 100 or on the display unit of the external device 100.

At step 920, the user is notified about the determined health care action to be performed, if the determined heath care action cannot be performed using the oral care device 100. The notification may be displayed on the display unit 606 of the oral care device 100 or on the display unit of the external device 800. The oral care device 100 is also configured to provide relevant recommendations to the user, for example but not limited to, general physician consultation, cancer specialist consultation, endodontist consultation, and general dentist consultation, among others. This information is displayed on the display unit 606 of the oral care device 100 or on the display unit of the external device 100.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the invention but as merely providing illustrations of some of the personally preferred embodiments of this invention. Thus, the scope of the invention should be determined by the appended claims and their legal equivalents rather than by the examples given.

What is claimed is:

1. An oral care device comprising:
    a head portion comprising:
        at least one supporting arm;
        a base, wherein the supporting arm extends from the base; and
        a sensor exposed from the supporting arm and the base, the sensor comprising
            at least one of an electromagnetic emitting source and an electrical energy emitting source and
            at least one of an electromagnetic energy detection mechanism and an electrical energy detection mechanism; and
    a handle portion, the head portion mounted on the handle portion, the handle portion comprising a processor, wherein the processor is configured to:
        receive signals from the sensor; and
        analyze the signals received from the sensor;
    wherein the at least one of the electromagnetic energy detection mechanism and the electrical energy detection mechanism is configured to detect reflected or scattered electromagnetic or electrical energy from at least one oral cavity tissue; and electromagnetic or electrical energy transilluminated from at least one oral cavity tissue or to detect electromagnetic or electrical energy transmitted from at least one oral cavity tissue to detect one or more of tooth demineralization, dental caries, tooth cavities, abnormal tooth surface color, inflammation or bleeding in gum, gingivitis, and periodontitis.

2. The oral care device as claimed in claim 1, wherein the head portion is mounted on the handle portion to allow for movement of the head portion relative to the handle portion.

3. The oral care device as claimed in claim 1, wherein the head portion comprises:
    a pair of the supporting arms, wherein the pair of supporting arms extend from the base to define a groove; and
    one or more cleaning elements, wherein each cleaning element is capable of being individually actuated; and
    a hygiene sensor for detecting one or more of residual particles of food, drink, smoke residue, plaque, and tartar.

4. The oral care device as claimed in claim 3, wherein the cleaning elements comprises plurality of sets of bristles and a dental floss, which are provided within the groove.

5. The oral care device as claimed in claim 4, wherein the dental floss is configured to move vertically along the supporting arms.

6. The oral care device as claimed in claim 5, wherein the dental floss is configured to move laterally, generally perpendicularly to the vertical movement of the dental floss.

7. The oral care device as claimed in claim 5, wherein the dental floss is offset relative to the sets of bristles, wherein the offsets prevents the dental floss from intersecting with the sets of bristles when the dental floss moves vertically or laterally.

8. The oral care device as claimed in claim 3, wherein the cleaning elements further comprises a tongue cleaner, wherein the tongue cleaner is provided on one of the supporting arms on a side opposite to the groove.

9. The oral care device as claimed in claim 3, further comprising an actuator configured to operate at least one of the cleaning elements, wherein the actuator is controlled by the processor.

10. The oral care device as claimed in claim 9, wherein the processor is configured to control operation of the at least one of the cleaning elements based on the analysis of the signals received from the sensor.

11. The oral care device as claimed in claim 3, further comprising a spacer component projecting from the supporting arm, wherein the spacer component is dimensioned to regulate pressure applied by one or more cleaning elements over one or more teeth of a user, or regulate distance of one or more of the cleaning elements over one or more teeth of the user.

12. The oral care device as claimed in claim 3, further comprising:
one or more of cleaning elements and a pressure sensor, wherein the pressure sensor is configured to enable detection of pressure applied by one or more of the cleaning elements on user's teeth; or
a motion sensor configured to enable detection of motion of the oral care device.

13. The oral care device as claimed in claim 1, further comprising a spacer component, wherein the spacer component is configured to prevent oral cavity tissues from rubbing against a portion of the sensor which is exposed towards the oral cavity tissues, or position the sensor at a distance from the oral cavity tissues, wherein the distance is based on distance required for desired functioning of the sensor.

14. The oral care device as claimed in claim 1, further comprising a spacer component projecting from the supporting arm, wherein the spacer component is positioned to interface with the gum of a user.

15. The oral care device as claimed in claim 1, wherein the sensor is selected from a group consisting of ultraviolet spectroscopic sensor, infrared spectroscopic sensor, visible spectroscopic sensor or a combination thereof.

16. The oral care device claimed in claim 1, wherein the sensor is a radio frequency sensor.

17. The oral care device as claimed in claim 1, wherein the sensor is a bioelectrical impedance sensor.

18. The oral care device as claimed in claim 1, wherein the processor is configured to enable wireless communication of information to an external device, wherein the information is based on the analysis of signals received from the sensor or one or more cleaning elements.

19. The oral care device as claimed in claim 1, wherein the analysis of the signals from the sensor enables determination of at least one health condition.

20. An oral care device comprising:
a head portion comprising:
at least one supporting arm;
a base, wherein the supporting arm extends from the base; and
a sensor exposed from the supporting arm; and
a handle portion configured to move relative to the head portion, the handle portion comprising a processor, wherein the processor is configured to:
receive signals from the sensor; and
analyze the signals received from the sensor;
a mounting wherein the head portion is mounted on the handle portion using the mounting for movement of the head portion relative to the handle portion,
an electrical cable, a signal cable and a power source, wherein, the electrical cable connects one or more cleaning elements or the sensor with the power source, while passing through the mounting between the head portion and the handle portion; and the signal cable connects one or more of the cleaning elements or the sensor with the processor, while passing through the mounting.

* * * * *